United States Patent [19]

Hu

[11] Patent Number: 4,944,676

[45] Date of Patent: Jul. 31, 1990

[54] REPLACEABLE FLUID FLOW CONTROL DEVICE FOR DENTAL UNITS

[76] Inventor: Chien-Hsiung Hu, No. 3-1, Alley 8, Lane 906, Minsheng E. Rd., Taipei, Taiwan

[21] Appl. No.: 308,611

[22] Filed: Feb. 10, 1989

[51] Int. Cl.⁵ .............................................. A61C 1/02
[52] U.S. Cl. ....................................... 433/98; 433/28; 433/100
[58] Field of Search ...................... 433/28, 84, 98, 100; 137/884

[56] References Cited

U.S. PATENT DOCUMENTS

| | | | |
|---|---|---|---|
| 3,638,310 | 2/1972 | Austin, Jr. ............................. | 433/28 |
| 3,991,473 | 11/1976 | Morgan ................................. | 433/28 |
| 4,151,647 | 5/1979 | Saupe et al. .......................... | 433/28 |
| 4,230,452 | 10/1980 | Austin, Jr. ............................ | 433/28 |

Primary Examiner—Cary E. Stone
Attorney, Agent, or Firm—Morton J. Rosenberg; David I. Klein

[57] ABSTRACT

A replaceable fluid flow control device having a first element for providing valve bodies and a second element for providing fluid inputs and outputs. The second element is firmly mounted on a dental unit with a pair of mounting rods, and the first element is engaged with the second element by screws. It is convenient to dismount the first element from the second element by detaching screws, while blockage occurs within the first element.

5 Claims, 4 Drawing Sheets

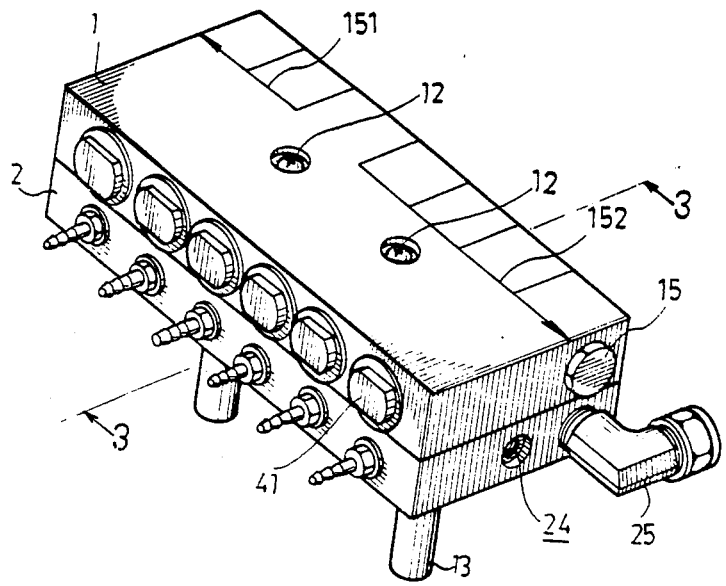

REPLACEABLE FLUID FLOW CONTROL DEVICE FOR DENTAL UNITS

BACKGROUND OF THE INVENTION

The present invention relates to a replaceable fluid flow control device for dental units, and more particularly relates to a replaceable water and air control device comprising a first means and a second means, in which a plurality of value bodies are provided in the first means, and a plurality of sets of fluid inputs and outputs are provided in the second means and respectively correspond the valve bodies.

In fluid flow control devices for dental units, it is generally recognized that the valve element for controlling the flow of the fluid is a fundamental element therein. Therefore, providing a valve means in the fluid flow control device in an accurate, reliable and inexpensive manner has been a primary objective of workers for several decades. Although great strides have been made, there remains a compelling need for an inexpensive valve control means which is easily replaceable.

All fluid flow control devices for dental units have two features in common—(1) a valve body for controlling the flow of fluids; and (2) a set of fluid inputs and outputs. Among conventional water and air controls, electromagnetic valves with relay or switch means are widely employed to control the fluid flow. The shortcomings in these type of devices with electromagnetic valve after long period of usage are as follows: (1) the insulator provided in the coil winding deteriorates because of high temperature; (2) due to insufficient voltage or unstable power supply, the performance of such devices is not efficient; and (3) such devices often suffer from leakage of electricity due to the use of electric controls. Moreover, only a single valve element with a fluid input and at least one fluid output is provided in such fluid flow control devices. A plurality of such control devices would therefore occupy much space.

A different approach to fluid flow control devices utilizes a valve to control fluid flow, which is controlled by a signal in the form of air pulses. As can be seen in FIG. 5, a conventional fluid flow control device 5 with a single valve element has a fluid input 51, a fluid output 52 and a valve-controlling input 53, all of which are integrally formed. When blockage occurs in the control device 5, it is impossible for the user to disassemble the control device to check and remove the trouble. Due to the integrated structure, the control device 5 must be replaced by a new one. Moreover, special tools are required to dismount the old control device and mount a new control device. This results in the interruption of the dental curing process.

The present invention has arisen from work in seeking to actually obviate and/or mitigate the above-mentioned drawbacks.

SUMMARY OF THE INVENTION

A primary objective of the present invention is to provide a replaceable fluid flow control device which comprises a first means for providing valve bodies and a second means for providing fluid inputs and outputs, wherein the first and second means are threaded together by screws. When blockage occurs on the valve portion of the first means, it is convenient to replace the old first means with a new one.

Another objective of the present invention is to provide a replaceable flow control device in which a plurality of valve bodies are provided to decrease its volume.

Still another objective of the present invention is to provide a replaceable fluid flow control device which can simultaneously provide various flow outputs of at least one fluid, corresponding different valve-control inputs.

Another objective of the present invention is to provide a replaceable fluid flow control device which has performance characteristics superior to any heretofore available.

These and additional objects, if not set forth specifically herein, will be readily apparent to those skilled in the art from the detailed description provided hereinbelow, with appropriate reference to the accompanying drawings.

DETAILED DESCRIPTION OF THE PREFERRED EMBODIMENT

Figure 1:
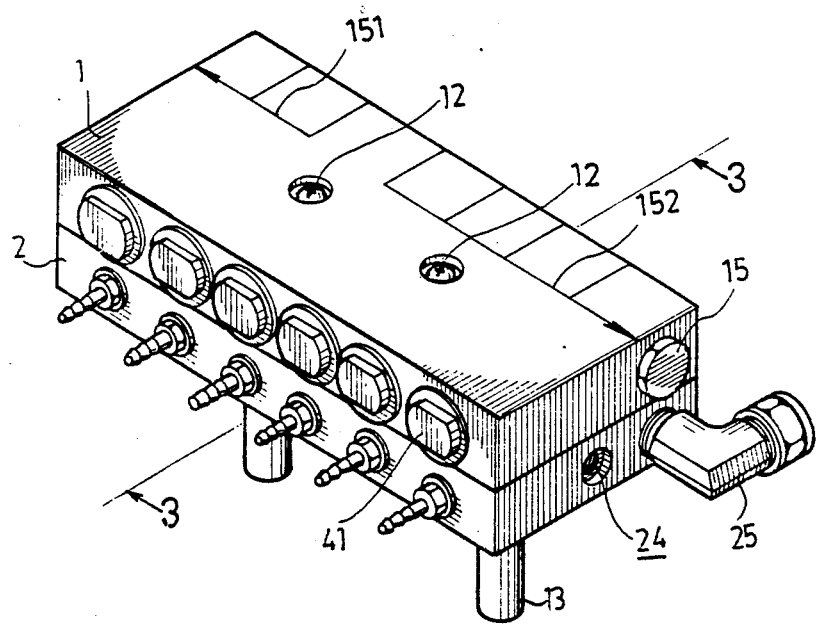
FIG. 1 is a perspective view of a replaceable fluid flow control device in accordance with the present invention.
Figure 2:
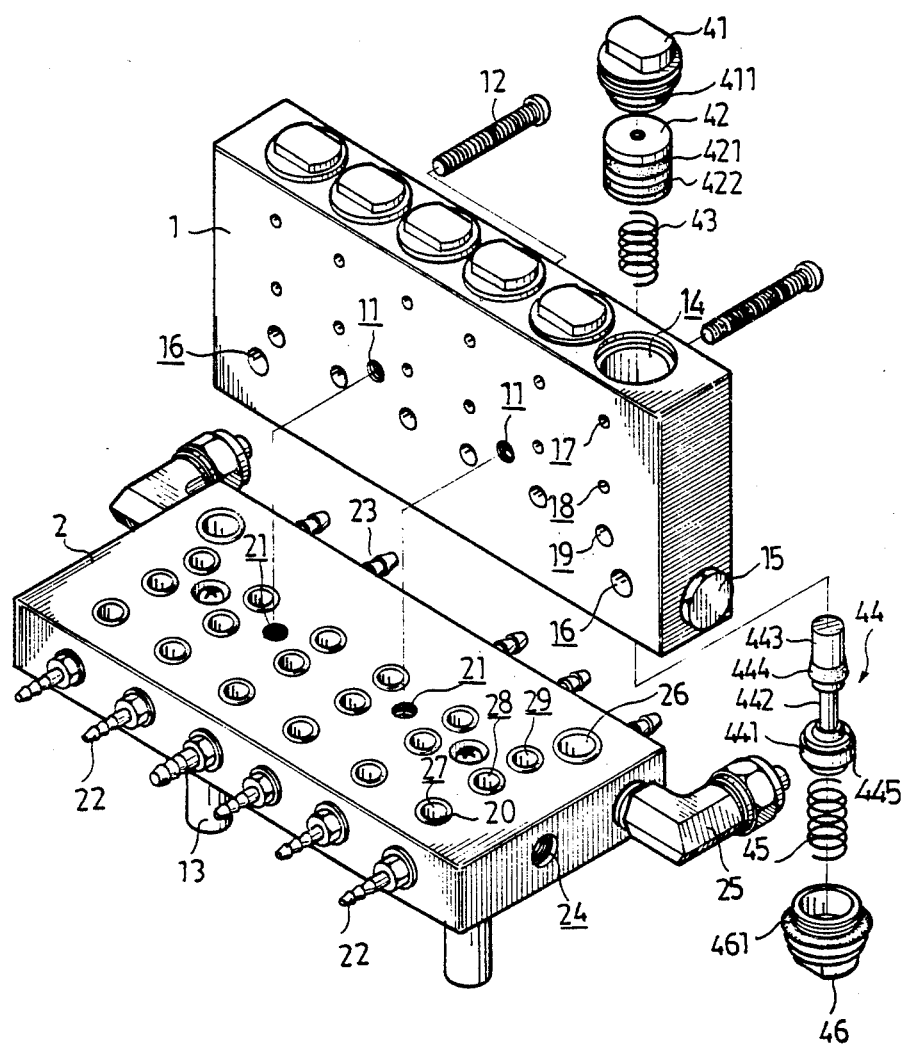
FIG. 2 is an exploded view of the replaceable fluid flow control device of FIG. 1.
Figure 4:
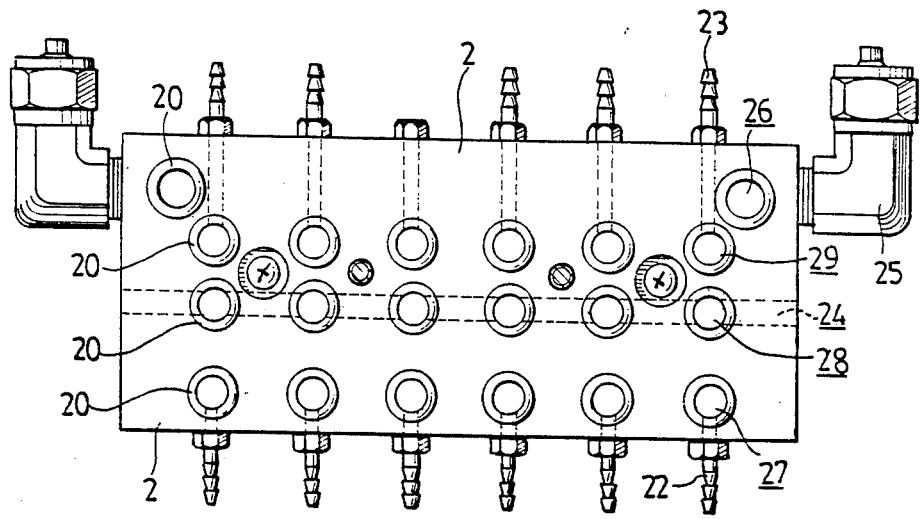
FIG. 4 is a perspective view of the upper surface of the second means of the replaceable fluid flow control device of FIG. 1, in which the channels provided within the second means are indicated in the dotted lines.
Figure 3:
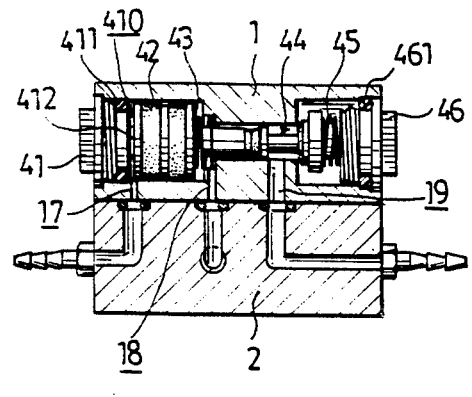
FIG. 3 is a cross-sectional view, taken along line 3—3 of FIG. 1.
Figure 5:
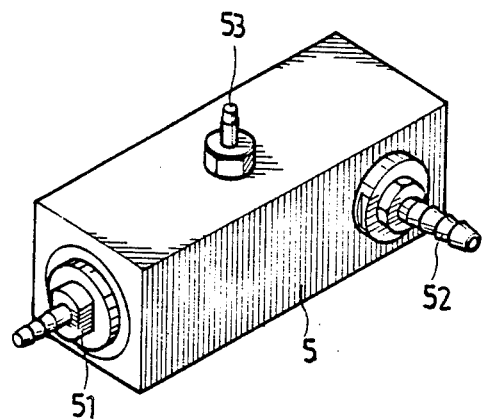
FIG. 5 is a perspective view of a conventional fluid flow control device.

Referring not to the drawings, and more particularly to FIGS. 1 to 4, it can be seen that a replaceable fluid flow control device in accordance with the present invention comprises a first means 1 and a second means 2 which is firmly mounted on a dental unit with a pair of mounting rods 13. Screw holes 11 and 21 are respectively provided on the first and second means 1 and 2 for receiving respective screws 12; therefore, it is convenient to dismount the first means 1 from the second means 2 by detaching screws 12 therefrom, while blockage occurs within the first means 1.

The first means 1 has a plurality of evenly spaced cylindrical bores 14 which extend lengthwise all the way through lateral sides of the first means 1. Each of the bores 14 comprises first, second and third portions of different radii, in which the second portions thereof have a shorter radius than those of the first and third portions. The first portion of each of the bores 14 sequently contains a first cap 41, a valve control sealing ring 42 and a first spring 43. A cone-shaped protuberance 412 (shown in FIG. 3) is formed on the inner side of the first cap 41 to define a space 410 between the first cap 41 and the valve control sealing ring 42. The valve control sealing ring 42 has a pair of axially spaced annular grooves to respectively receive V-shaped or U-shaped sealing rings 421 and 422 in a manner that the two V-shaped sealing rings are disposed side by side. The second portion substantially contains a valve body 44 which comprises a head 441, a stem 422 and a retarding end 443. The third portion contains a second spring 45 and a second cap 46, in which the second spring 45 urges the head 441 of the valve body 44 against the interface of the second and third portions to prevent the intercommunication therebetween. Moreover, O-rings 445 and 444 are respectively provided on one side of the head 441 proximate to the stem 442 and on the circumferential surface of the retarding end 443 to effect a water-proof seal respectively between the second and third portions and between the first and second portions. The first and second caps 41 and 46 have respective O-rings 411, 461 thereon to prevent any fluid within the bore 14 from leaking therefrom.

The third portions of part of adjacent the bores 14 are intercommunicated to one another by a respective fluid-supply channel from each end side of the first means 1. As can be seen in FIG. 1, for example, the left-side and right-side fluid-supply channels 151 and 152 are indicated in solid lines shown on the upper surface of the first means. The right-side fluid-supply channel 152 communicates four bores 14 provided on the right side of the first means and is blocked by a bolt 15. A result of the respective fluid-supply channels 151 and 152 is that the fluid flow control means of this invention can afford various fluid outputs of different fluids, for example, air, water or the like.

On the lower surface of the first means 1, a first supply hole 16 is provided corresponding to and communicating with each of the fluid-supply channels 151 and 152; likewise, a first air-input hole 17, a first air-output hole 18 and a first access hole 19 are provided corresponding to and communicating with each bore 14. The first air-input hole 17 is provided in a position corresponding to the space 410 formed between the first cap 41 and the valve control sealing ring 42. The first air-output hole 18 and the first access hole 19 are communicated with the second portion, in which the former is proximate to the first portion and the latter is proximate to the third portion.

The first supply holes, air-input holes, air-output holes and access holes 16, 17, 18 and 19 respectively correspond to second supply holes, air-input holes, air-output holes and access holes 26, 27, 28 and 29 which are provided on upper surface of the second means 2 with respective sealing rings 20 provided on uppermost ends thereof to prevent leakage between the first and second means 1 and 2. All of the second air-output holes 28 are intercommunicated by a second channel 24 extending lengthwise all the way through to the end sides of the second means 2. On one lateral side of the second means 2, a plurality of input ports 22 are provided to communicate with the respective second air-input holes 27 for compressed air input to actuate the valve body 44. On the opposite lateral side thereof, a plurality of output ports 23 are provided to communicate with the respective second access holes 29 for fluid output corresponding to the action of the respective input ports 22. A connector 25 is provided on each end side of the second means 2 to communicate with the second supply hole 26 for fluid input.

For the sake of simplicity, the operation of the valve body 44 is only illustrated in one bore, with respect to its corresponding input port 22, since the operation of all the valve bodies 44 are the same. When the input port 22 is supplied with the compressed air input, the compressed air fills in the space 410 via the second air-input hole 27 and the first air-input hole 17. Since the first V-shaped sealing ring 421 is leak-proof, the compressed air within the space 410 urges the valve control sealing ring 42 against the first spring 43, and subsequently urges the valve body 44. Further against the second spring 45, the valve control sealing ring 42 then actuate the valve body 44 toward the third portion. The movement of the valve body 44 results in the second portion being communicated with the third portion. Therefore, the fluid filled in the third portion via the fluid-supply channel is introduced into the first access hole 19, and then exhausts through the second access hole 29 and its corresponding out port 23. In order to prevent the fluid from entering the space 410, the second V-shaped sealing ring 422 is provided on the valve control sealing ring 42, and the valve body 44 further comprises the O-ring 444 to retard the fluid from entering the first portion. The first air-output hole 18 is provided proximate to the first portion to release the fluid or the air filled around the first spring 43 to facilitate the movement of the valve control sealing ring 42.

While the present invention has been explained in relation to its preferred embodiment, it is to be understood that various modifications thereof will be apparent to those skilled in the art upon reading this specification. Therefore, it is to be understood that the invention disclosed herein is intended to cover all such modifications as fall within the scope of the appended claims.

I claim:

1. A replaceable fluid flow control means for dental units, comprising a first means and a second means which are engaged together by at least two screws;

said first means having a plurality of cylindrical bores which extend lengthwise through lateral sides of said first means; each of said bores having first, second, and third portions of different radii; said first portion receiving a first spring, a valve control sealing ring and a first cap; said third portion for receiving a second spring and a second cap; and said second portion for receiving a valve body disposed between said first and second springs; a number of said third portions of adjacent said bores being intercommunicated to one another by a respective fluid-supply channel from each end side of said first means;

a first supply hole being provided on lower surface of said first means communicating with said fluid-supply channel; a first air-input hole communicating with said first portion of each said bore; a first air-output hole proximate to said first portion and a first access hole proximate to said third portion being provided thereof communicating with said second portion of each said bore;

a second supply hole, air-input hole, air-output hole and access hole being provided on an upper surface of said second means, and respectively corresponding to said first supply hole, first air-input hole, first air-output hole and first access hole for each said bore; a sealing ring being provided on an uppermost end of all holes on said second means to prevent leakage between said first and second means;

a connector being provided on each end side of said second means to communicate with said second supply hole for fluid input; all of said second air-output holes being intercommunicated by a second channel extending lengthwise all the way through said end sides of said second means;

a plurality of input ports being provided on a lateral side of said second means to communicate with said respective second air-input holes for compressed air input to actuate said valve body; a plurality of output ports being provided on a second lateral side of said second means to communicate with said respective second access holes for fluid output; and said compressed air causing said valve control sealing ring to actuate said valve body; a movement of said valve body making said first channel communicate with said first access hole to output fluid supplied from said respective connector.

2. A replaceable fluid flow control means for dental units as recited in claim 1, wherein said valve body comprises a head, a stem and a retarding end; said head has an O-ring thereon and said retarding end has an O-ring on a circumferential surface thereof to effect a water-proof seal respectively between said second and third portions, and between said first and second portions.

3. A replaceable fluid flow control means for dental units as recited in claim 1, wherein said valve control sealing ring has a pair of axially spaced annular grooves to respectively receive sealing rings.

4. A replaceable fluid flow control means for dental units as recited in claim 1, wherein said first cap has a cone-shaped protuberance on an inner side thereof to define a space between said first cap and said valve control sealing ring.

5. A replaceable fluid flow control means for dental units as recited in claim 1, wherein said first and second caps have respective O-rings thereon to prevent fluid within said bore from leaking therefrom.

* * * * *